United States Patent
Zur

Patent Number: 5,842,989
Date of Patent: Dec. 1, 1998

[54] ARTIFACT REDUCTION IN MAGNETIC RESONANCE ANGIOGRAPHIC IMAGES

[75] Inventor: Yuval Zur, Fort Collins, Colo.

[73] Assignee: Elscint, Ltd., Haifa, Israel

[21] Appl. No.: 619,003

[22] Filed: Mar. 21, 1996

[51] Int. Cl.$^6$ .................................................. A61B 5/055
[52] U.S. Cl. ........................ 600/410; 600/419; 324/306
[58] Field of Search .................................. 600/410, 419; 324/306, 309

[56] References Cited

U.S. PATENT DOCUMENTS

| | | |
|---|---|---|
| 4,644,280 | 2/1987 | Paltiel . |
| 4,947,837 | 8/1990 | Sano et al. . |
| 4,949,041 | 8/1990 | Zur . |
| 5,016,637 | 5/1991 | Koizumi et al. . |
| 5,035,244 | 7/1991 | Stokar . |
| 5,199,435 | 4/1993 | Sugimoto et al. . |
| 5,335,660 | 8/1994 | Dumoulin . |
| 5,363,844 | 11/1994 | Riederer et al. . |
| 5,436,562 | 7/1995 | Dumoulin . |
| 5,655,531 | 8/1997 | Nishimura et al. . |

OTHER PUBLICATIONS

"Respiratory Ordered Phase Encoding (ROPE): A Method for Reducing Respiratory Motion Artifacts in MR Imaging" by D.R. Bailes et al., Jul./Aug 1985.

"The Design of Variable Tip Angle Slab Selection (TONE) Pulses for Improved 3–D MR Angiography" by David Purdy et al., Society of Magnetic Resonance Abstracts, p. 882, 1992.

"Three–Dimensional Time–of Flight MR Angiography Using Selective Inversion Recovery RAGE with Fat Saturation and ECG Triggering: Application to Renal Arteries" by Debiao Li et al., Magnetic Resonance Med., vol. 3, pp. 414–422, 1994.

Primary Examiner—Marvin M. Lateef
Assistant Examiner—Shawna J. Shaw
Attorney, Agent, or Firm—Fenster & Company Patent Attorneys, Ltd.

[57] ABSTRACT

A magnetic resonance angiography method for acquiring angiographic images using any or all of three different types of selective presaturation pulses to the particular parts of the body for enhancing vascular imaging. The three types are:

1) an inversion pulse applied prior to the application of a burst of RF pulses used for tipping the spins designed to eliminate signals from unwanted blood entering the field of view being imaged, 2) inversion pulses applied between the first inversion pulse and the first of the Rf pulses used to suppress blood not properly suppressed by the first type of suppression pulses, such as fast flowing blood, and 3) saturation pulses applied within the burst of RF pulses to suppress signals from slow flowing blood when in the 2D acquisition mode. Special heart and breath gating methods are also described that enable good compromises between image quality and scan time.

22 Claims, 8 Drawing Sheets

ARTIFACT REDUCTION IN MAGNETIC RESONANCE ANGIOGRAPHIC IMAGES

FIELD OF THE INVENTION

This invention is concerned with magnetic resonance imaging (MRI) and more particularly with using magnetic resonance methods and equipment for imaging blood in the vascular system.

BACKGROUND OF THE INVENTION

The magnetic resonance phenomena has been used for magnetic resonance angiography (MRA). Magnetic resonance equipment is well suited for imaging blood vessels since it overcomes some of the problems encountered when using X-Ray methods. Specifically, MRI is non-invasive, non-ionizing, and does not require any contrast substance.

Most of the body tissues in a section of the body being imaged are static. However, blood in the sections of the body being imaged is moving and, therefore, it is being replaced by blood from parts of the body that are not being imaged; i.e. from parts of the body that have not experienced an RF excitation pulse.

This difference is utilized in prior art MRA. To take advantages of this difference in blood and static body tissue in MRA, a selective inversion pulse (preferably an adiabatic fast passage pulse) is first applied to the patient in the MRI magnetic field. After a period Ti, a burst of radio frequency (RF) pulses is applied. After each of the RF pulses in the burst, a signal is acquired responsive to read gradient pulses which are configured to generate gradient echoes. The acquired signal is phase encoded by appropriate phase encoding pulses applied after each RF pulse within the burst. The read gradient pulses and the phase encoding pulses cooperate so that each RF pulse of the burst of pulses generates a signal sufficient to fill a line in the K plane or K volume, depending on whether 2D imaging or 3D imaging is being accomplished. In addition to the described pulse sequence, the prior art blood imaging arrangements included either heart gating and/or breath gating. The gating was designed to reduce motion artifacts.

It should be understood that in blood imaging arrangements there are many problems including the artifacts caused by motion. Among the other problems is that the blood itself is pulsating in the arteries and in addition to the blood pulsating the vascular vessels are moving in different parts of the body where breathing, for example, causes movement of the blood vessels. Further, there are different characteristics of the blood vessels in different parts of the body. For example, in the brain there is no movement of the blood vessels and the pulsitility of the blood in the arteries is exceedingly small since the body is designed to provide the brain with a constant supply of blood rather than a pulsating blood supply. In the thorax region, on the other hand, breathing has a definite adverse effect on the images of blood vessels, because of the breathing motion. In addition to motion caused problems, for example, in the abdomen section there are a plethora of blood vessels including large and small blood vessels that overlap and follow serpentine paths.

Each of these different characteristics require different approaches to the imaging procedure. Gating subjects the acquisition period to time windows. For example, the gating usually is set up so that the imaging is only accomplished during dilation of the heart. The time limitation on the acquisition period is further reduced by breath gating since only a portion of the breathing cycle is used for acquisition. Also because of the plethora of blood vessels it is necessary to selectively look at the blood vessels. Therefore, pulse sequences must selectively discriminate between arteries and veins, for example, and between fast flow and slow flow. Pulses causing saturation must be spatially selectively applied. Over all, the system must take into account the heart beat pulsations and movement caused by such things as breathing.

Blood imaging is either accomplished by using two dimensional procedures or three dimensional procedures. Advantages of three dimensional procedures compared to two dimensional procedures is a higher signal to noise ratio and less susceptibility to motion. Less susceptibility to motion comes about because most of the signal is acquired during the relatively short time period when phase encoding gradient pulses have low amplitudes. Motion occurring during phase encoding gradient pulses of high amplitudes have a much smaller affect on the image. A distinguishing characteristic of 3D imaging relative to 2D imaging is that in 3D imaging slow flow and small blood vessels are not seen.

Thus, using the prior art MRA systems and methods there are problems caused by pulsitility due to the heart beat, breathing and other involuntary body motion, overlapping veins, and arteries, differences between slow flow and fast flow.

In the prior art the burst of RF pulses comprised RF pulses with varying tip angles suppression pulse such as a as a function of time to compensate for signal decay. Thus the tip angles were varyingly increased during the time of application of the pulses. That is, the first tip angle may have been 15° for example, a second tip angle 17°, and third tip angle 19° etc. until the number of tip angles in the burst is used up. The tip angles were only time dependent in the prior art.

SUMMARY OF THE INVENTION

The invention provides improved methods of MRA. The improved methods require discrimination by the operator i.e., operator interaction. Among other things, the improved methods use heart gating, but only where necessary. For example, heart gating is not necessary in the imaging of the brain. However when imaging the thorax or legs, heart gating is necessary and is used. The preferred arrangements for MRA, herein also provide greater suppression of body tissue and unwanted blood signals in addition to using methods that allow greater flexibility with regard to the motion due to patient breathing and its effects on acquisition time and image quality. More particularly, the operator can vary the acquisition time relative to the quality of the image being taken. Thus, the image information is looked at and if the quality is not good enough, then the operator causes the imaging system to acquire more data and thus take more time. If the quality is sufficient, or better than the quality of applicable standards, then the operator can reduce the time of acquisition.

Also according to the inventive MRA system, the tip angles are varied not only as a function of time but also as a function of space in the 3D imaging.

Further according to the present invention unwanted blood signals are more completely suppressed using different types of suppression. For example one type of suppression is the use of selective inversion pulse applied to either the ROI or the VOI. In addition, selective saturation is achieved between the inversion pulse and the first RF pulse of the RF burst. In addition, the operator takes into account where the blood is coming from and applies saturation pulses to those areas from which unwanted blood signals enter the VOI or the ROI.

Another type of suppression is accomplished in 2D imaging by applying saturation pulses during the burst of RF pulses.

In accordance with a preferred embodiment of the present invention, a method of magnetic resonance angiography is disclosed; the method comprises:

placing a subject in a large static magnetic field, applying a first selective suppression pulse such as a saturation pulse, said first selective suppression pulse such as a saturation pulse being a selective inversion pulse to suppress magnetic resonance signals in selected locations including a location that is being imaged;

acquiring signals from fresh blood flowing into the location that is being imaged;

said acquiring step comprising:

applying a burst of selective RF pulses, applying phase encoding pulses between the RF pulses of the burst of selective RF pulses, sampling the gradient echo signals generated due to each RF pulse of the burst of selective RF pulses, and applying further selective saturation pulses to suppress unwanted signals from the location being imaged.

Another feature of the invention is that almost no recovery time is allotted between detection and the following suppression pulse such as on inversion pulse, so that the body regions being studied achieve a quasi-steady state of saturation. During a substantial part of the steady state, in the saturated ROI or VOI the difference between the spin vector of the long T1 blood tissues and the short T1 of the static body tissues i.e. fat is small because the whole location being imaged is saturated, whereas fresh magnetized blood that enters the ROI or VOI provides relatively large signals. Therefore:

(a) blood vessels are more clearly observed (greater blood tissue contrast);

(b) a fat saturation pulse prior to the burst of RF pulse is not needed;

(c) there are less ghostly artifacts due to breathing because the signal from body tissues is saturated; and (d) data acquisition is less sensitive to variations in the cardiac rhythm.

A combination of the capability of utilizing the maximum available portion of the breathing cycle and the reduction of the time restraints of the pulse sequence allows for more data to be acquired and therefore the imaging is acquired in less time.

The 3D MRA imaging is specifically used to acquire arterial images. The VOI is subjected to an inversion pulse thereby repressing the static body tissue and the blood tissue that is in the VOI. The source of arterial blood (i.e. the heart) is outside the VOI and therefore the arterial blood entering the VOI is unsuppressed and in sharp contrast to the suppressed static tissue and blood in the VOI. A volume from which blood whose signals are not wanted flows into the VOI is saturated between the inversion pulse and the detection pulses that are applied to the VOI to suppress the unwanted signals. Since slower arterial blood could become saturated when traversing a large slab, slower arterial blood is imaged using multi-slab VOI's.

The 2D MRA is used to acquire images of the slow flowing blood of the arteries or veins. The region of interest is subjected to an inversion pulse. In addition, the source of unwanted blood; for example, arterial blood is suppressed when venous blood is being imaged. Among other ways of suppressing the arterial blood is by subjecting the heart to a saturation pulse. Thus, the static tissue of the ROI and arterial blood going into the ROI are suppressed while new venous blood coming into the ROI, is unsuppressed.

When 2D MRA is used to image arterial blood then the ROI is suppressed along with a region from which venous blood enters the ROI. The static tissue of the ROI, the blood in the ROI and the venous blood flowing into the ROI are all suppressed while arterial blood flowing into the ROI is unsuppressed. In 2D imaging techniques in general, slices of the ROI are kept thin and saturation pulses are applied between the inversion pulses and the detection pulses. In general consecutive slices are imaged. Saturation pulses are also applied during the bursts of RF pulses to help eliminate signals from blood that is not of interest. The system described requires judgement on the part of the operator as to where to apply suppression and where in the breathing cycle and in the heart cycle to acquire data.

The advantages of the various aspects of the invention are:

(a) high contrast resulting in good visualization of blood vessels;

(b) removal of artifacts due to breathing and pulsatile blood flow;

(c) ability to image either veins or arteries;

(d) ability to image slow blood flow;

(e) ability to trade image quality for imaging time;

(f) removal on limitations of patient breathing; and (g) relative insensitivity to cardiac rhythm.

These and other advantages and features of the invention vis-a-vis the prior art will be best understood when considered in the light of the following description of exemplary embodiments of the invention made in conjunction with accompanying drawings; wherein:

GENERAL DESCRIPTION

Figure 1:
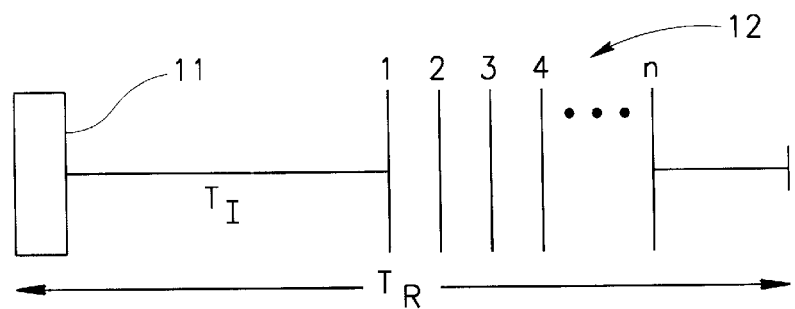
FIG. 1 shows the basic pulse sequences of the inventive magnetic resonance angiography.
Figure 2:
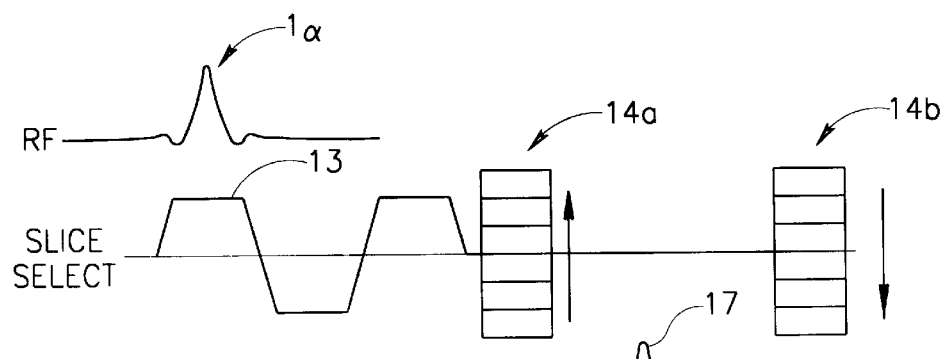
FIG. 2 shows details of the basic pulse sequence of FIG. 1.

The basic pulse sequence used in accordance with the inventive angiography imaging system herein is shown in FIGS. 1 and 2. A suppression pulse such as an inversion pulse 11 is applied to the region of interest (ROI) and data is acquired TI seconds after this pulse. In this way the inversion pulse suppresses signals from the static tissue. During TI fresh blood enters the ROI. This blood is fully magnetized and therefore its signal is very strong. Accordingly, the contrast between blood and tissue is maximized. Data is acquired by applying a burst 12 of n RF pulses, where each pulse in the burst is preferably applied in conjunction with a gradient echo sequence of pulses. Phase encoding pulses (not shown) are also applied in the usual spin warp sequence manner. The gradients in this gradient echo sequence are motion compensated (first and zero moment nulled) as is known in the art and as shown in FIG. 2.

The whole sequence is repeated every TR sec. For each burst of n pulses, n lines on k-space are acquired and the sequence is repeated until the k-space is filled up and the desired number of averages is complete.

As shown in FIG. 2 one of the Rf pulse of burst 12 is applied to tip the spins by α degrees during the application of a slice select gradient 13. Encoding gradients 14a and 14b are added in the slice select direction when a 3D acquisition is desired. The in-plane phase encoding gradient lobes 50a and 50b are used to encode the echo signal 17. The tip angle α varies from one Rf pulse to the other within a given burst. A gradient echo generating read gradient 16 is applied and the RF echo signal 17 is acquired.

At least two types of scans are used:

1.) 3D scans, where a thick slab of a few centimeters is excited and an encoding lobe 14 in the slice select direction is added as shown in FIG. 2.

2.) 2D scans, where one slice is excited each time, and the whole slab is scanned by scanning the slices sequentially. In this case, the encoding lobe in the slice select direction is omitted and the rf pulse is modified to excite a very thin slice each time, rather than a thick slab.

With 3 scans the encoding gradient along the slice direction is varied within each burst of n RF pulses, while the in-plane phase encoding gradient is incremented from one TR to another but remains constant within each burst.

Presaturation Pulses

Figure 3:
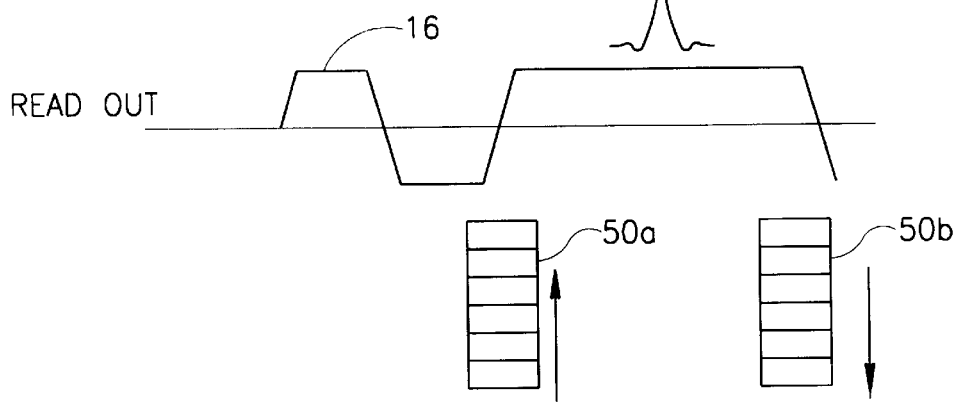
FIG. 3 illustrates the application of an inversion pulse used as a type 1 presaturation pulse applied to a schematic showing of a torso.
Figure 3:
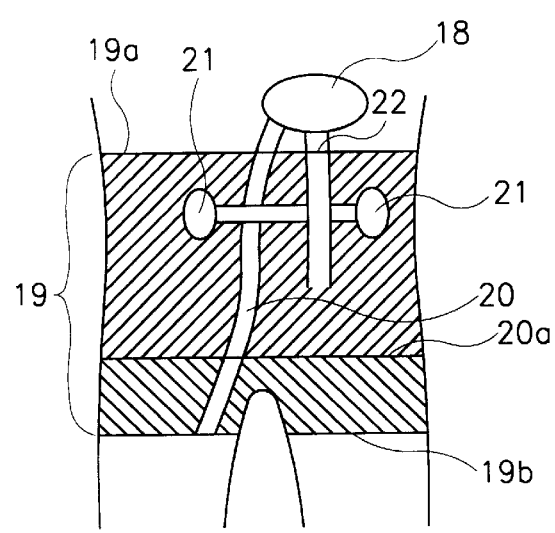

There are a very large number of blood vessels within the body and its extremities. Each scan is designed to look only at one specific type of blood vessel. For example, there are scans that are designed to acquire data on arteries and to suppress data from veins. In another scan, data from the portal vein is desired and data from other blood vessels such as arteries, renal veins and veins in the digestive system are suppressed. Therefore unique means and methods are used that enable the spatial suppression of data from unwanted vessels by using spatially selective rf presaturation pulses. These suppressive presaturation pulses are divided into three types, each type is spatially independent from the other types. The location of any saturation band is controlled by applying one of the presaturation pulses at the proper frequency in conjunction with an appropriate slice selective gradient pulse. The three presaturation pulse types differentiated by where and when they are applied are:

1.) A first type of saturation pulse is where the spatial width and location of the inversion pulse itself is designed so as to suppress unwanted blood as shown in FIG. 3 wherein the object is to suppress data of blood from veins below the heart 18 and to emphasize data from arterial blood in the renal arteries. This is accomplished by applying an inversion pulse that is spatially defined by the area 19 extending from 19a to 19b as shown in FIG. 3 and waiting a time TI before acquiring signals. The signal from the veins such as the vena cava 20 and from static tissue in the kidneys 21 is suppressed whereas signals of arterial blood coming from the heart through the aorta 22 is not affected.

Figure 4:
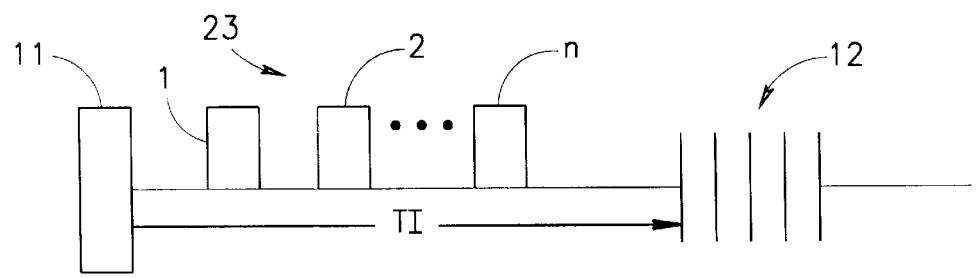
FIG. 4 illustrates the second type of presaturation pulse applied between the inversion pulse and the burst of RF pulses of the basic pulse sequence.

2.) A second type of presaturation pulses are additional (and spatially independent) m presaturation Rf pulses 23 that are applied during TI between the inversion pulse 11 and the burst of n pulses 12 as shown in FIG. 4. The purpose of these pulses is to suppress any data from blood vessels that was not suppressed or not adequately suppressed by the inversion pulse 11. For example, the fast flowing blood coming from the vena-cava 20 is not adequately suppressed by the inversion pulse 11. Therefore a type 2 presaturation band defined by lines 20a and 19b is placed below the kidneys as shown in FIG. 3 to suppress signals from the vena-cava by using the Rf presaturation pulses 23, applied during TI.

Figure 5:
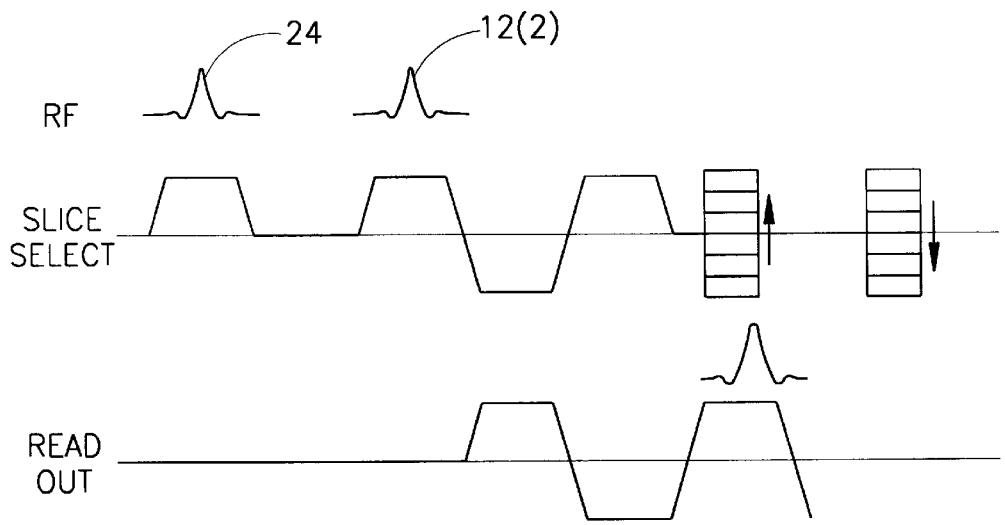
FIG. 5 illustrates the third type of presaturation pulse applied within the burst of RF pulses.

3.) A third type of presaturation pulses are those applied within the burst of n pulses. These pulses are necessary to suppress the signal of slow flowing blood when using a 2D acquisition mode. These presaturation pulses saturate blood flowing from locations that are independent of the presaturation pulses of types 1) and 2). Each presaturation pulse 24 of type 3 is applied in conjunction with the regular selective imaging pulse such as pulse 12 (2) and gradient echo sequence as shown in FIG. 5. There is preferably one presaturation pulse, such as pulse 24, for each of the n rf pulses in the burst 12 of rf pulses.

Figure 6:
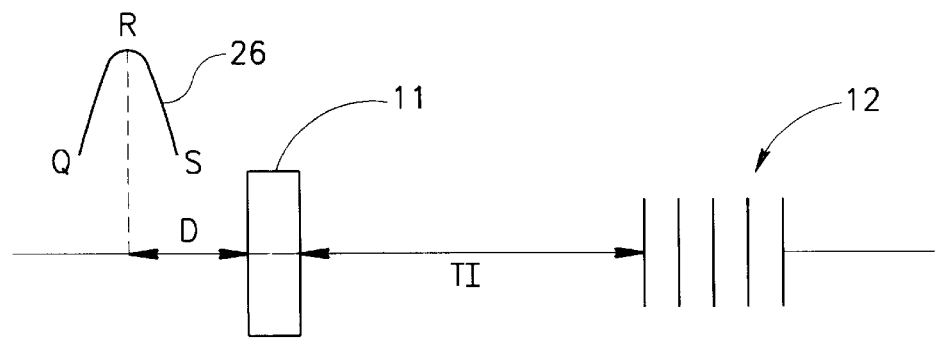
FIG. 6 illustrates the basic pulse sequence synchronized to the R wave from an ECG.

Reduction/Elimination of Motion Artifacts Due to Breathing and Due to Pulsatile Blood Flow The pulse sequence shown in FIGS. 1 and 2 is synchronized to the R wave or QRS signal 26 from an ECG of the heart as shown in FIG. 6. Once the R-wave 26 of the ECG is detected, the inversion pulse is applied D sec. later. Usually D is close to zero so that the inversion pulse is applied immediately before or during the heart contraction. During TI fresh blood flows into the ROI. The sampling period (burst of n pulses) occurs during diastole, where blood flow is laminar and non-pulsatile. The time window where blood flow is laminar in the large vessels (aorta, aortic arch, renal arteries and extremity arteries) is about 150–200 ms. The time TI allotted for fresh blood to flow into the region of interest is about 200–300 ms. The TR of the sequence equals the R—R interval (approx. 600–1000 ms). With this TI and TR there is excellent suppression of data from static tissue independent of T1 values. Even for fat which has a short T1 of approximately 300 ms, suppression by a factor of more than 10 is obtained.

Figure 7:
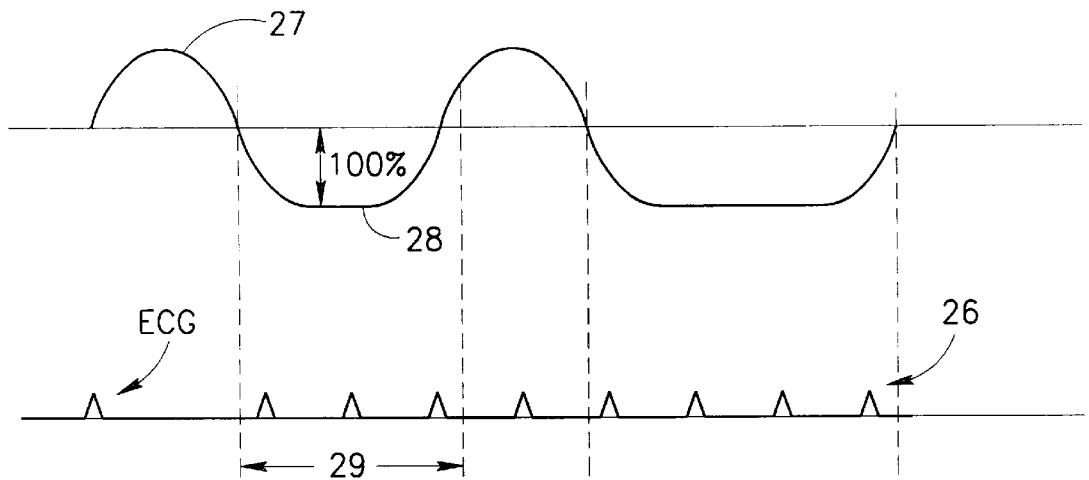
FIG. 7 is a graph of the breath cycle to illustrate the complete range of breathing amplitudes during the ECG cycles.

Minimization of breathing motion artifacts is done by running the sequence of FIG. 6, but acquiring data only from those TR's that occur when the breathing motion amplitude is within a certain predetermined range of values as explained below and as shown in FIG. 7. The breathing motion of the patient is monitored via a respiration belt or any other known means. The breathing motion is sampled by the computer over many breathing cycles, and the computer determines the average breath-in and breath-out amplitudes.

During each ECG cycle the system determines whether the MR signal is acquired or not depending on the breathing amplitude. Usually those ECG cycles that occur within the breath-out period 29 are acquired, since during this time the breathing amplitude is relatively small. However, the operator may determine to sample ECG cycles where the amplitude is less than 100% of the breath-out amplitude. In this case more cycles of ECG are discarded resulting in longer scan time, but image quality improves because the variations in breathing amplitudes are smaller. To further save time, the system determines whether to sample the data for that ECG cycle, immediately before the data acquisition window and not immediately after detection of the R-wave.

Figure 8:
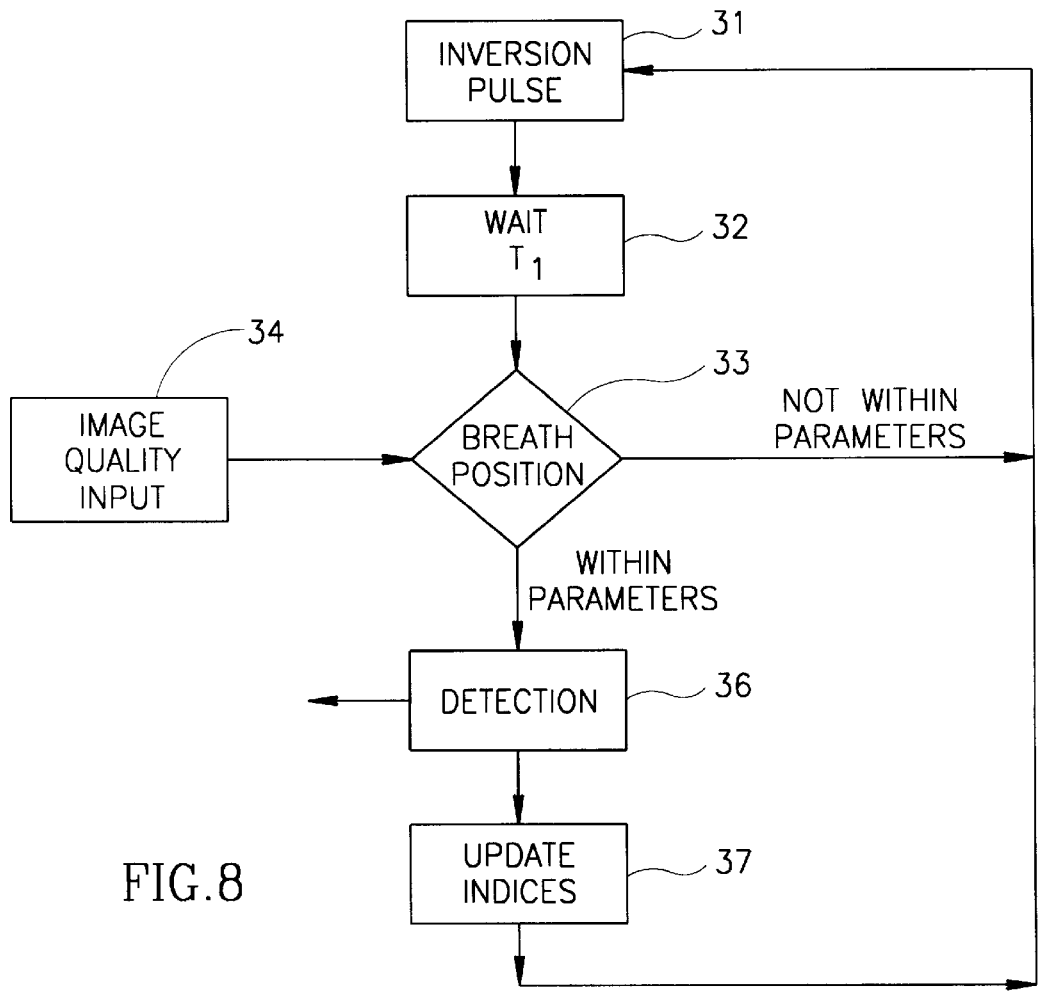
FIG. 8 is a flow chart showing how the operator decides on sampling data during the breath cycle to choose between scan time and image quality.

A flow chart is shown in FIG. 8. The inversion pulse 11 is first applied as shown in block 31. After the waiting time TI as indicated in block 32, the position of the subject's thorax as indicated by block 33 is considered in order to determine whether the breath position is within the specified parameters. The operator's image quality input, indicated by block 34, helps to determine the desired parameters. If the position of the thorax is not within the parameters the system does not acquire the data. If the thorax position is within the parameters the signal is detected and added to the other detected signals as indicated by block 36 and 37.

To further reduce breathing artifacts, the phase encoding within a breathing acquisition window are reordered (as known in the art for "COPE" or "ROPE"; (see an article D. R. Bailes et al entitled "Respiratory Ordered Phase Encoding (ROPE): A Method for Reducing Respiratory Motion Artifacts in MRI Imaging" J. Comp Assist. Tomog. Vol. 9 pp. 835–838 (1985), so that a given phase encoding gradient amplitude is applied only when a specific breathing amplitude (within the allowed window) is detected.

Breathing artifacts are significantly reduced with the imaging sequences presented herein as a direct result of the excellent static tissue suppression obtained by the described sequences. Breathing artifacts are caused by signals from static tissue and especially from fat which usually has high signal amplitudes. With this sequence even fat is significantly suppressed and breathing artifacts are greatly reduced.

Use of Variable RF Flip Angles to Enhance Signal to Noise Ratio

A problem in blood imaging is that as detection progresses, the signal from the blood gets weaker. To solve this problem and to enhance signal to noise ratio (SNR), a flip angle $\alpha i$ of the i-th RF pulse within the burst 12 is calculated by a computer program. In this manner the spins are fully magnetized and emit a constant signal from the first Rf pulse in a burst with tip angle $\alpha 1$ to the last Rf pulse in that burst with tip angle $\alpha n$. This enables the application of relatively large flip angles without having to worry about the signal from the blood oscillating. Accordingly, the variable tip angle eliminate artifacts while increasing SNR. The variable tip angles also enable the use of phase encoding gradients with small amplitudes (where most of the signal is generated) with the Rf pulses used at the beginning of the burst (with tip angle $\alpha 1$). It is at the beginning of the Rf burst that the signal of the static tissue is the weakest (due to the inversion pulse TI sec. earlier). This fact further improves the contrast between blood and static tissue.

Figure 9:
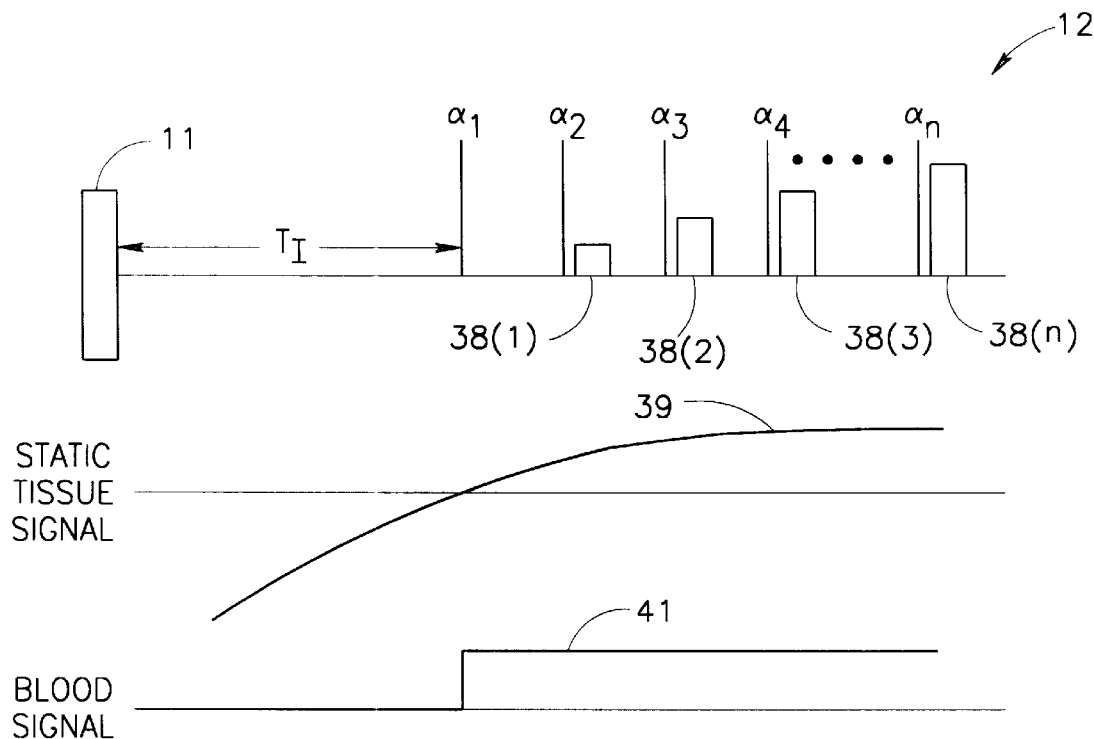
FIG. 9 illustrates the use of variable flip angle pulse sequence to obtain maximal blood/tissue contrast.

The variable flip angle pulse sequence is demonstrated in FIG. 9. The maximal blood/tissue contrast occurs after $\alpha 1$, where the phase encoding pulse amplitude is zero. The phase encoding pulse amplitudes are shown at 38(1), 38(2), 38(3) and 38(n) in FIG. 9.

The values of the flip angles $\alpha 1$ to $\alpha n$ were optimized for blood spins that remain within the excitation slab all during the time of the burst of Rf pulses 12. However, some fast flowing blood passes through the slab and feels only a small number of Rf pulses.

Figure 10:
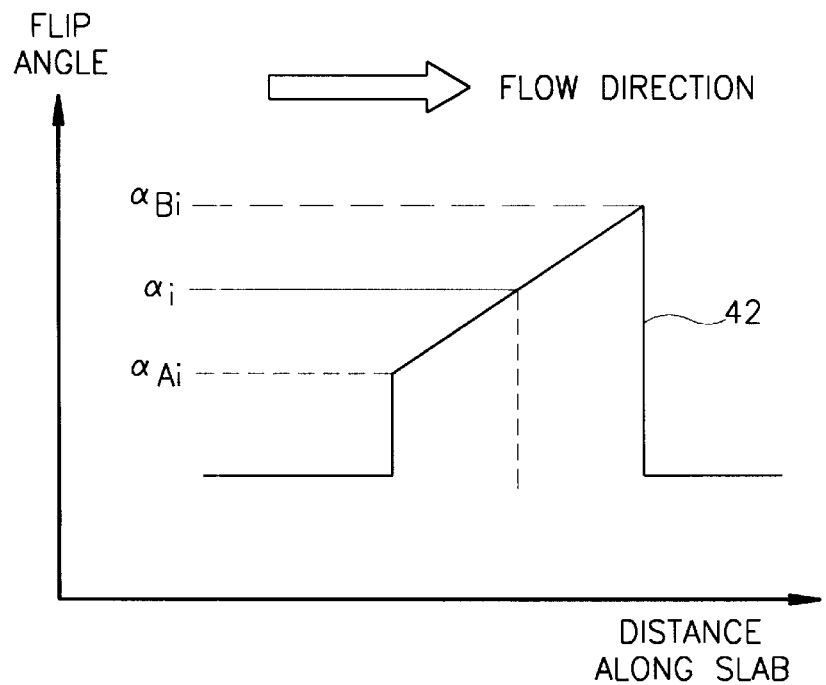
FIG. 10 illustrates a slab profile obtained using the variable flip angle sequence of FIG. 9.

To further enhance the signal of fast flowing blood, the slab profile is assigned to be position dependent as shown in FIG. 10. This is done as known in the art. See the abstract by D. Purdy et al in the Society of Mag. Res. Abstracts, P.882, (1992) where the Rf pulses are the inverse Fourier transform of the slab profile. The slab is designed such that (as shown in FIG. 10) spins that enter the slab feel a smaller flip angle, and as they travel inside the slab they experience an increasing flip angle so as to increase the signal they emit. FIG. 10 shows the slab profile 42 of Rf pulse $\alpha i$ in FIG. 9 whose average flip angle along the slab is $\alpha i$, but its flip angle varies along the slab from $\alpha Ai$ to $\alpha Bi$. Thus, during the burst of RF pulses 12 the flip angle varies in time from $\alpha 1$ to $\alpha n$: (usually between 15°–40°). Also, each Rf pulse i has a slanted slab profile so that the pulse flip angles vary within the slab (spatially) from $\alpha Ai$ to $\alpha Bi$. For example, a pulse with $\alpha i=20°$; has $\alpha Ai=16°$ and $\alpha Bi=24°$.

Figure 11:
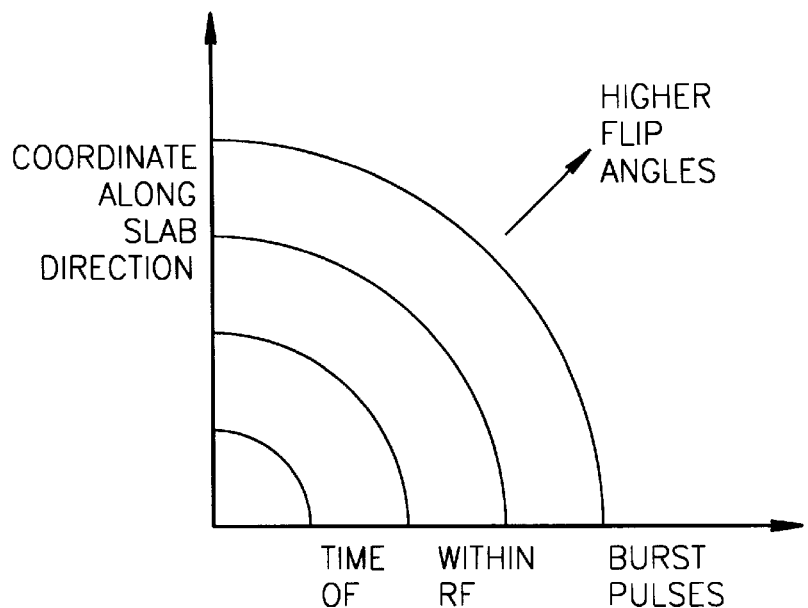
FIG. 11 is a graph showing contours of the tip angles which are varied both as a function of time and spatial position.

FIG. 11 shows a contour representation of the flip angles as a function of both time and space so that the detected signal magnitudes will stay relatively constant. Flip angle variability depends on blood flow characteristics; therefore different body regions require different schemes for varying the flip angles.

Elimination of Artifacts Associated With Presaturation Pulses

As mentioned before, there are three types of presaturation pulses:

1.) the inversion pulses, per se
2.) inversion or saturation pulses applied during TI; and
3.) Saturation pulses applied in conjunction with each pulse in the burst 12 of RF pulses.

A presaturation pulse excites (and consequently saturates) any desired band at any desired location by using a transmitter frequency f1 in conjunction with a slice select gradient of amplitude G such that $\gamma GZ_1/2\pi=f1$. In this way the desired presaturation band location Z1 is determined. If the frequency band width of the presaturation pulse is $\Delta f$ then the width of the presaturation band $\Delta Z$ is $\gamma GZ/2\pi=\Delta f$, where $\gamma$ is the gyromagnetic ratio (4.257 KHz/Gauss for proton nuclei). When a band at frequency f1 and location Z1 is saturated while a slice is also excited and imaged at frequency f and location Z the sequence shown in FIG. 12 is applied.

Figure 12:
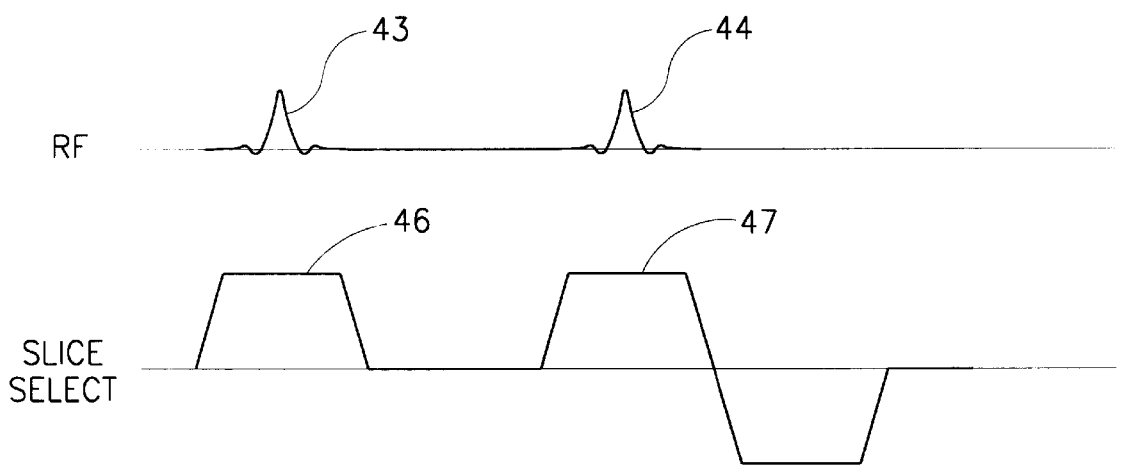
FIG. 12 is used to show how artifacts are generated using the type 3 presaturation pulses.

A presaturation pulse 43 at frequency f1 and an excitation pulse 44 are shown in FIG. 12. Slice select gradient pulses 46, 47 operate in conjunction with the RF pulses 43 and 44, respectively. The location Z of frequencies f are related by the equation $\gamma GZ/2\pi = f$ where $\gamma$ is the gyromagnetic ratio. The presaturation slab is excited only by the presaturation pulse (at f1) and the excitation slab is excited only by the excitation pulse 9 at f). However, the X-Y magnetization from f1 is detected by the readout gradients of the gradient echo sequence that follows the excitation pulse. This detected signal Mxy from the slice at frequency f1 generates very strong artifacts because usually the f1 slice is very thick (3–10 cm) whereas the f slice may be very thin (about 2mm). A conventional way to eliminate these artifacts is to add large gradient lobes (5–10 ms long) between the presaturation pulse and the excitation pulse. For the presaturation pulse of types 1) and 2) the artifacts can be eliminated because: a) these presaturation pulses are applied at least 40–50 ms prior to the signal sampling. Therefore, this unwanted Mxy signal decays due to T2 relaxation time. b) there is enough time; and to insert large gradient lobes of 10–15 ms, that spoil these unwanted signals.

For presaturation pulses of type 3) spoiler gradients cannot be used because, the sequence is very time limited (the number of pulses in a burst is limited by a sampling window of 160 ms, for example. The decay of the unwanted signals due to T2 relaxation does not occur because the presaturation pulses are very close in time to the excitation pulses.

Figure 13:
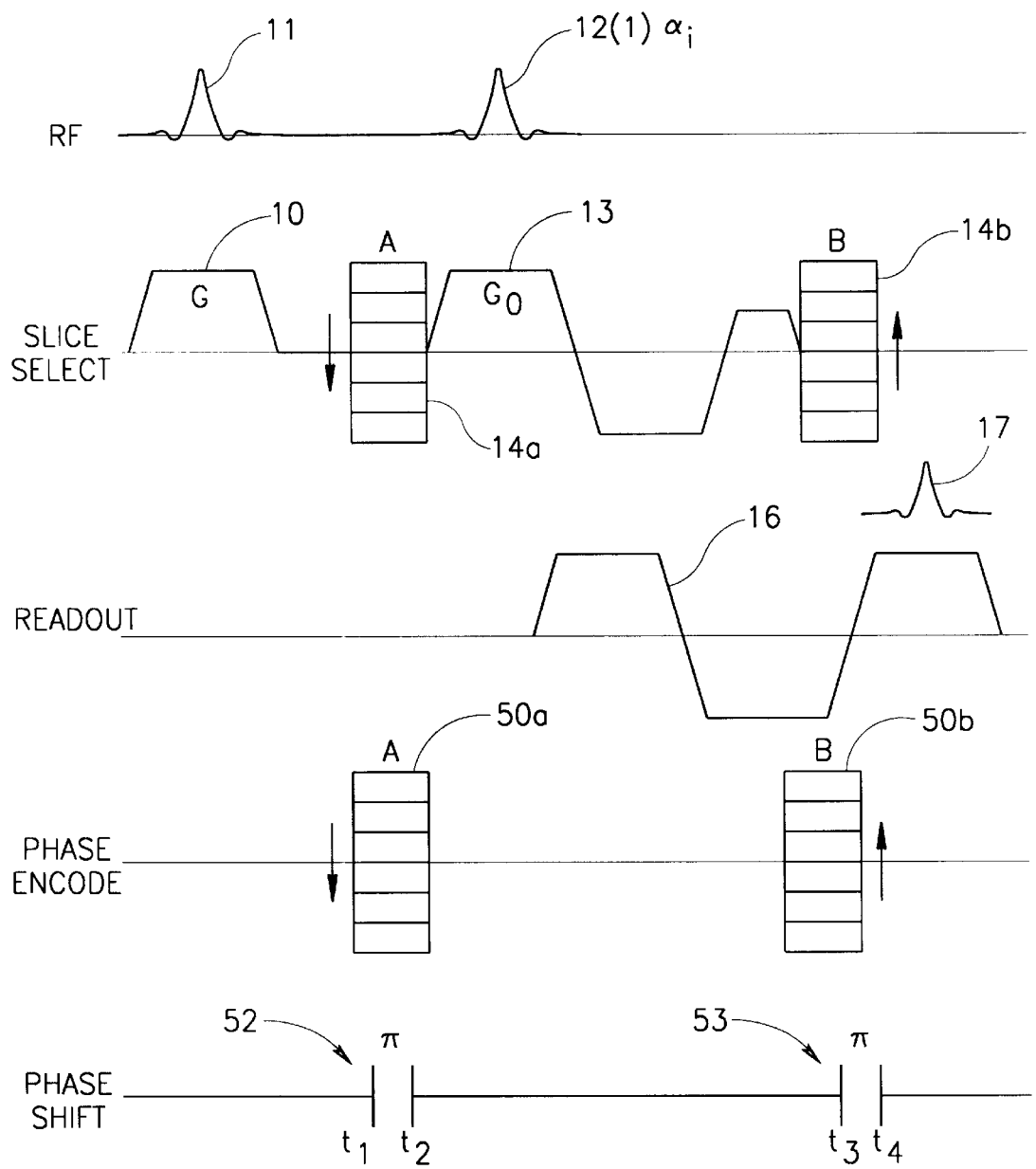
FIG. 13 illustrates how the artifacts of FIG. 12 are significantly reduced.
Figure 14A:
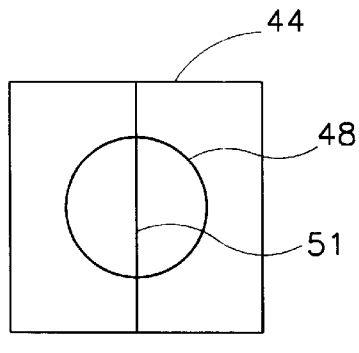
FIGS. 14a and 14b show the effects on the image of the sequence of FIG. 13.
Figure 14B:
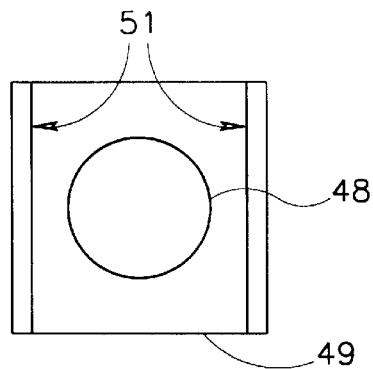

To solve these problems arising with the use of type 3 saturation pulses the sequence as shown in FIG. 13 is used. If the pulse sequence of FIG. 13 is compared to that of FIG. 2, it is seen that the phase encoding gradient lobe 50a and the phase encoding gradient lobe in the slice select direction 14a in FIG. 2 were transferred in FIG. 13 to be prior to the excitation pulse αi (12(1)) and between the presaturation pulse 11 and excitation pulse αi. The presaturation pulse 11 of FIG. 13 is shown applied during the application of select gradient pulse 10. Now the Mxy magnetization from the presaturation pulse 11 at frequency f1 is encoded by the phase encoding lobes A (50a and 14A in the slice select direction), but it is deencoded (that is, the encoding is cancelled) by lobes B (50b and 14b in FIG. 13). Therefore, during sampling the unwanted magnetization is unencoded and appears in the image 48 on screen 49 as a single line 51 (in FIG. 14a) along the readout direction at Y=0 (where Y is the phase encoding direction). The wanted signal from the excitation pulse αi is encoded as usual by phase encoding lobe B. To remove the line artifact from the center of the image, a phase shift is generated on the phase encoding phase encoding gradients of lines A and B as shown at 52 and 53 in FIG. 13. These phase shifts are performed every other phase encoding line. The unwanted signal from the presaturation pulse is unaffected by the phase shifts since the total shift=π+π or 360° whereas the desired signal from the excitation pulse is shifted π at every other phase encoding pulse. After acquisition the signals are shifted by π radians at every other phase encoding pulse with software. The end result is that the unwanted line 51 at Y=0 is shifted by half a field of view to the image's edge, whereas the desired signal appears as a normal image. This effect is demonstrated in FIGS. 14a and 14b. FIG. 14a is without the 180° phase shift while FIG. 14b is the image with the 180° phase shift. Of course, when only 2D imaging is required the phase encoding lobes 14a and 14b in the slice select direction shown on FIG. 13 are eliminated. The pulse sequence in FIG. 13 precludes the need to use spoiler gradients for the presaturation pulses, and enables the use of presaturation in conjunction with every pulse 12 in the Rf burst without increasing the acquisition time. The elimination of presaturation pulse artifacts is complete and robust.

It should be noted that the method of eliminating artifacts as explained with regard to FIGS. 13 and 14 can be applied in any gradient echo imaging sequence used in the elimination of blood signals.

Use of a Small Number of Phase Encoding Steps

Figure 15A:
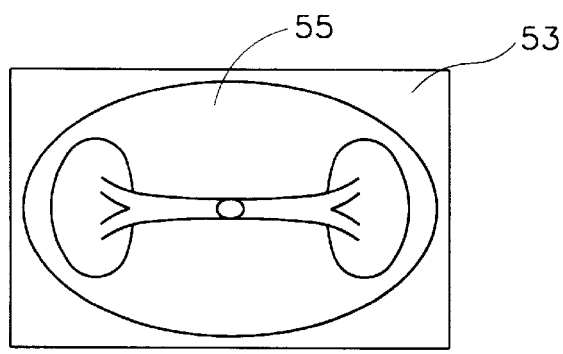
FIGS. 15a and 15b illustrate the use of a smaller field of view made possible by the excellent background suppression.
Figure 15B:
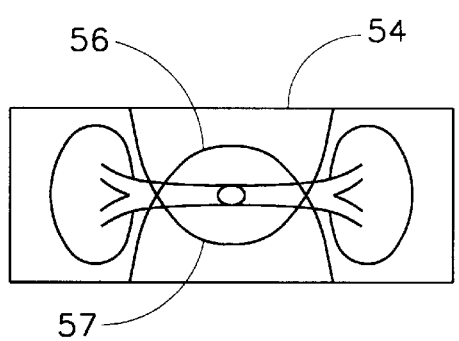

It is important to reduce scan time, especially when respiratory synchronization is used. With the angiography technique described herein scan time can be reduced by using fewer phase encoding due to the excellent background suppression. This is demonstrated in FIGS. 15A and 15B. FIG. 15A shows typical axial image 53 in the region of the kidneys using the usual 20×20 cm field of view. The abdomen, 55, in FIG. 15A is fully shown with this large field of view. The region of the renal arteries occupies only a small fraction of the abdomen. If static tissue suppression is very good, a limited field-of-view, such as the 8×20 cm view 54 of FIG. 15B can be used. However, when suppression is not good aliasing artifacts of the abdominal wall shown by lines 56, 57 spoil the image with the smaller field of view. When the suppression of data is good enough such as in the procedures described herein, then the aliasing of tissue into the imaging field-of-view is small enough to be non-consequential. If abdominal aliasing is ignored (because the abdominal tissue signal is suppressed) a field of view 54 of 8×20 cm can be used, rather than the conventional 20×20 cm view 53. Therefore, if a resolution of 1 mm is required in the phase encoding direction, only 80 encodings are required rather than the 200 encodings that would be needed if abdominal tissue aliasing was a problem. In this way imaging time is reduced.

3D Angiography

Figure 16:
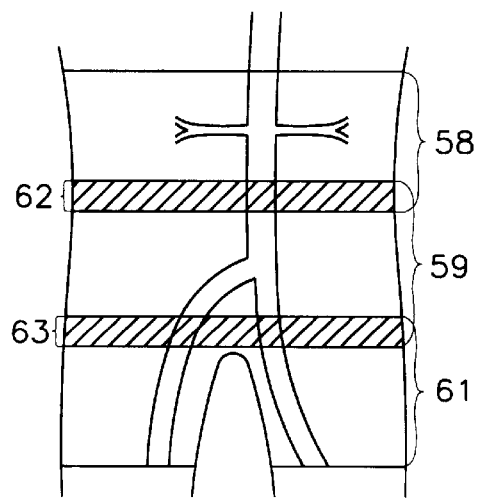
FIG. 16 illustrates multi-slab scanning with overlap for use when images of larger anatomical regions are required.

When fast flowing blood is imaged, fast flow usually occurs in arteries, 3D angiography is used. The big arteries in the body (i.e. aorta, renal arteries, aortic arch, carotid arteries, hepatic arteries etc.) are imaged with 3D. The pulse sequence in FIGS. 1 and 2 is used. The venous data is removed by applying an inversion pulse on the veins and a type 2) presaturation pulse on the vena-cava as shown in FIG. 3. Fresh blood from the heart is unaffected whereas data from static tissue and veins are suppressed. Breathing synchronization and cardiac gating is used for the renal arteries and for other arteries in the abdomen. For the aortic arch, carotid arteries and iliac arteries only cardiac gating is used. The slab width is about 5–6 cm. Multi-slabs and overlap are used when an image of a larger anatomical region is required. This is demonstrated in FIG. 16. As explained above about 80 phase encodings are used for a limited field-of-view in the phase encoding direction. For the multi-slab scans of FIG. 16, data from one slab is acquired in a given time and the data from the other slabs are acquired sequentially one after the other with the slabs overlapping. Thus, in FIG. 16 data from slab 58 is first acquired followed by data from slabs 59 and 61 sequentially. The overlap regions are shown as 62 and 63. Usually the phase encoding gradient in the slice direction is varied within the burst of n RF pulses (and n echoes). The phase encoding gradient itself is also varied from one burst to another.

As an example; suppose a 256×80×64 3D data set is wanted; where the 256 data points are in the readout direction, 80 data points are in the phase encoding direction and 64 data points are in the slice direction. In each burst we acquire 16 phase encodings in the slice direction. Therefore 4 bursts are required to acquire 64 encodings in the slice direction. For each 64 slice encodings we acquire 1 encoding in the Y-direction (phase encoding direction). Hence, we need 4×80=320 bursts (or 320 heart beats) to acquire this slab.

Sequential 2D Multislice Angiography

In this mode thin and contiguous 2D slices are sequentially acquired. The slice width is typically about 2 mm. In this mode there is no phase encoding in the slice direction. Because each slice is very thin, saturation of flowing blood is minimal. Therefore, the saturation of unwanted blood signal is difficult to accomplish and type 3) presaturation pulses must be used (see FIG. 5) to suppress undesired signals from in-flowing blood. Type 3) pulses are very efficient in suppressing undesired slow flowing blood because they are applied immediately before the Rf excitation pulse (see FIG. 5) and because they are applied with a very short TR within the RF burst.

Figure 17:
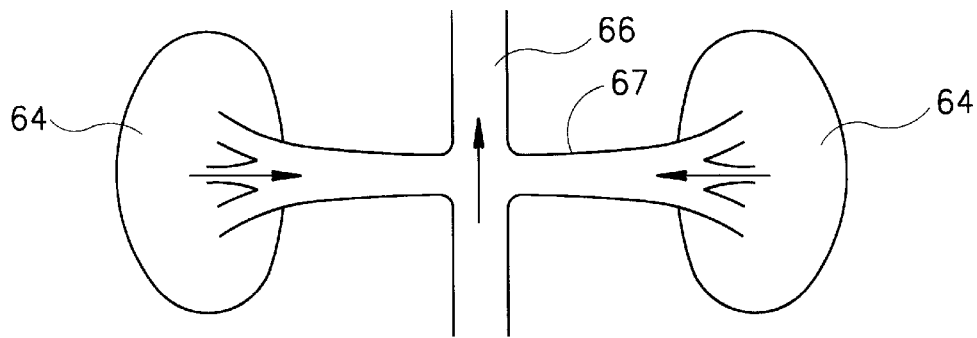
FIG. 17 illustrates venal blood flow source being in an organ.
Figure 18:
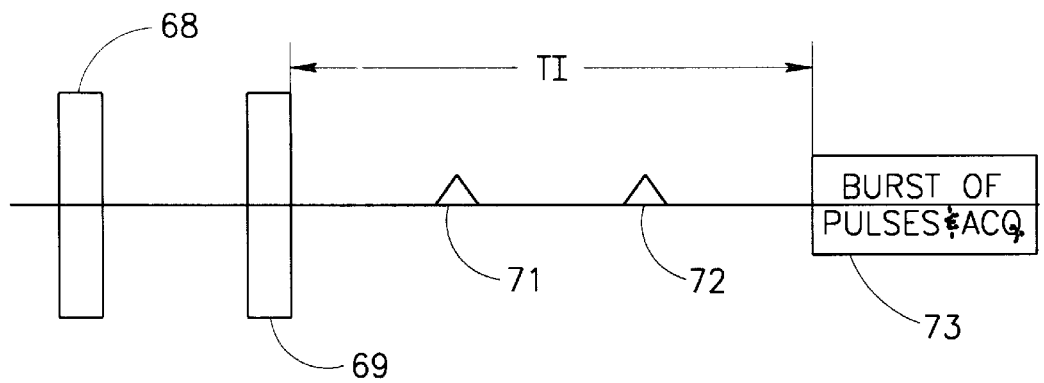
FIGS. 18 and 19 respectively show a pulse sequence using the three types of presaturation pulses and where they are applied.

Acquisition of sequential 2D slices is usually the only possible mode of acquisition for imaging blood flowing in veins. This is due to the fact that the source of flow for veins is from within the anatomical organ being scanned. An example is shown in FIG. 17 where the venous blood in the kidneys is shown. Flow is from the kidney 64 itself to the vena-cava 66 through the renal veins exemplified at 67. Thick excitation slabs or inversion pulses on the kidneys cannot be used because the source of flow would be suppressed. Therefore in this mode the adiabatic inversion pulse shown in FIG. 1 is applied only on the thin slice we want to image. Arterial blood is suppressed by applying an adiabatic inversion pulse on the heart immediately after the first inversion pulse (which suppresses static tissue only within the slice). This is shown in FIG. 18 where adiabatic inversion pulse 68 is applied to suppress static tissue within the slice being scanned. Pulse 68 is followed by adiabatic inversion pulse 69 applied on the heart to suppress the arterial blood signal. Then type 2) presaturation pulses such as pulse 71 and 72 are applied prior to the application of the burst of pulses as indicated at 73. The user decides how many presaturation pulses and of what type are to be used. In this way unwanted blood signals that come from different sources and from different directions can be suppressed. The disadvantages of sequential 2D slice acquision is the fact that a movement of the patient at any time within the scan causes a slice to be shifted in position from all the previous slices and this causes a serious artifact.

An Example of a 2D Sequential Acquisition of the Renal Veins

Figure 19:
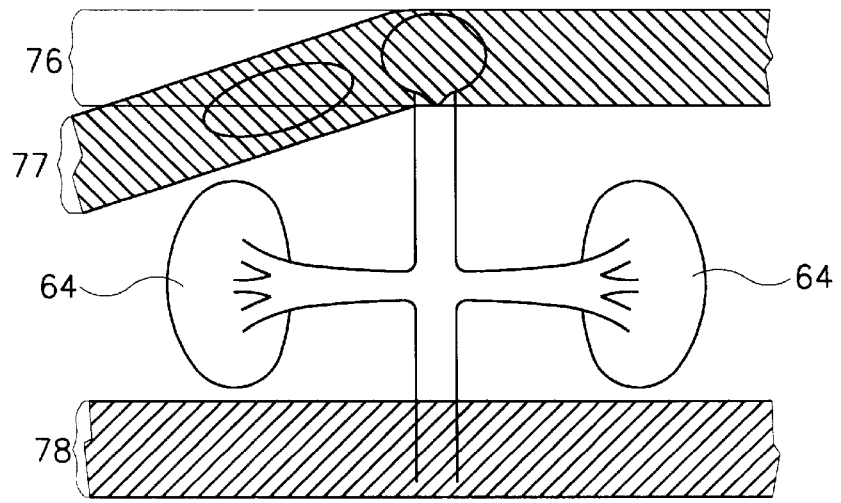

This example is shown in FIG. 19. The kidneys 64 are scanned slice after slice sequentially and the static tissue within each slice is suppressed by the first adiabatic inversion pulse 68 shown in FIG. 18. The inversion pulse 69 is applied to areas which cover the heart and suppresses arterial blood data. The type 2) presaturation pulses 71 and 72 are applied to the areas 77 which covers the liver to suppress data from blood flowing from the liver. The type 3) presaturation signals are applied to cover the area 78 to suppress data from blood flowing from the digestive system.

2D vs. 3D Angiography

The advantages of using 3D angiography are:

1.) the signal to noise per unit time is high because all the volume is continuously excited throughout the scan, and 2.) most of the magnetic resonance signal is acquired during the relatively short time when the slice and the in-plane phase encoding gradients are approximately zero. Therefore, if the patient does not move during this (relatively) short time, a good image is acquired.

For 2D angiography with consecutive slices, a movement of the patient during any time in the scan causes a misalignment artifact between the slices. The disadvantage of 3D angiography is the saturation of blood which is excited over a thick slab. Therefore, when fast moving blood signal is desired (that is arterial blood) 3D multi-slab acquisition is used, whereas for slow moving blood, (that is veins) usually 2D multislice angio is used.

Advantages and Improvements Over Prior Art

The advantages and improvements of this sequence over prior art such as the article by D. Li et al entitled "Three-Dimensional Time-of-Flight MRA Using Selective Inversion Recovery RAGE with Fat Saturation and ECG Triggering: Application to Renal Arteries", published in Mag. Res. Med. Vol 3 pp. 414–422 1994 include:

1) The ability of this procedure to eliminate breathing artifacts by using a special breath gating and phase encoding reordering technique.

2). The ability of the procedure explained herein to suppress slow flowing blood and therefore to acquire artifact-free angiograms with the 2D sequential multi-slice technique. The slow flowing blood is suppressed by type 3) presaturation pulses.

3). The ability of this procedure to selectively or collectively image arteries and/or veins.

4.) The ability of this procedure to selectively suppress blood signals in a few directions and locations simultaneously by applying type 1) type 2) and type 3) presaturation pulses.

5.) The ability of this procedure to significantly reduce scan time by using a limited field-of-view in the phase encoding direction because the near ideal suppression of static tissue signal so that static tissue signal aliasing is inconsequential.

6.) The excellent blood/tissue contrast obtained using this procedure so that even fat signal is significantly suppressed. Therefore, no fat-suppression Rf pulse is needed.

The invention can be applied to many MRA techniques and is not limited to the particular technique described above. More particularly, it will be appreciated by those skilled in the art that the present invention is not limited by what has been described herein. Rather, the scope of the invention is defined only by the claims that follow.

I claim:

1. A method of magnetic resonance angiography (MRA) for imaging a portion of a subject comprising:

placing said subject into a strong static magnetic field;

measuring breathing caused movement of said subject;

applying an inversion pulse to said subject synchronized to said subjects heart beat; and measuring radiation emitted from said subject only if measured breathing caused movement is within a given set of values.

2. A method of magnetic resonance angiography (MRA); said method comprising:
   placing a subject in a large static magnetic field,
   applying a first selective saturation pulse,
   said first selective saturation pulse being a selective inversion pulse to suppress magnetic resonance signals in selected locations including a location that is being imaged;
   acquiring signals from fresh blood flowing into the location that is being imaged;
   said acquiring step comprising:
      applying a burst of selective RF pulses at a time TI after the application of said first selective saturation pulse,
      applying phase encoding pulses between RF pulses of the burst of selective RF pulses,
      acquiring a gradient echo signal generated due to each of the RF pulses of the burst of selected RF pulses, and
      applying further selective saturation pulses during said time TI to suppress unwanted signals from locations not being imaged.

3. The method of MRA of claim 2 wherein said step of applying further selective saturation pulses to suppress unwanted signals from the locations not being imaged comprises:
   applying a presaturation pulse immediately prior to said burst of selective RF pulses,
   applying a select gradient simultaneously with the application of said presaturation pulse.

4. The method of MRA of claim 3 wherein said select gradient selects the location not being imaged for presaturation.

5. The method of MRA of claim 3 wherein said select gradient pulse selects the region from which blood flows into the region being imaged when the signal from said inflowing blood is not wanted.

6. The method of MRA of claim 3 wherein said step of applying further selective saturation pulses to suppress unwanted signals from the location not being imaged comprises:
   applying at least one selective saturation pulse between the selective RF pulses of the burst of RF pulses.

7. The method of MRA of claim 2 including the step of breath gating.

8. The method of MRA of claim 7 wherein the step of breath gating includes determining the time taken by an average breathing cycle, determining an average breathing cycle movement, controlling the portion of the breathing cycle during which signals are acquired to enable the control of quality of the image in a trade off between quality and acquisition time.

9. The method of MRA of claim 7 wherein said gating including acquiring signals gated to the heart cycle, said gating step including controlling the gating so that signals are acquired while the heart is expanding.

10. A method of magnetic resonance angiography (MRA) for imaging blood flow in a portion of the subject, said method of MRA comprising:
   placing the subject in a large static magnetic field,
   supplying a first selective pulse to suppress unwanted magnetic resonance signals in selected locations including a location that is being imaged,
   acquiring signals from fresh blood flowing into the location that is being imaged,
   said acquiring step comprising:
      applying a burst of selective Rf pulses,
      applying phase encoding pulses between the Rf pulses of the burst of selective Rf pulses,
      sampling echo signals after each Rf pulse of the burst of selective pulses, and
      applying further selective saturation pulses to suppress unwanted signals from the location being imaged.

11. The method of MRA of claim 10 including using two dimensional procedures.

12. The method of MRA of claim 10 including using three dimensional procedures.

13. The method of MRA of claim 10 including using heart gating.

14. The method of the MRA of claim 10 including using breath gating.

15. The method of claim 10 wherein the RF pulses of said burst of RF pulses have tip angles varied as a function of both time and space.

16. The method of claim MRA of claim 14 wherein breath gating includes the step of varying acquisition time relative to the quality of the image being taken.

17. The method of the MRA of claim 15 including the step of varying the tip angles as a function of time as well as a function of space in 3D imaging.

18. The method of the MRA of claim 10 wherein the step of applying further selective pulses includes the step of applying saturation pulses between said first selective pulse and said first Rf pulse of said burst of Rf pulses.

19. The method of the MRA of claim 18 wherein said steps of applying further selective saturation pulses comprises the step of applying at least one saturation pulse during the burst of Rf pulses in 2D imaging.

20. The method of the MRA of claim 10 wherein time to recover between detection and the next first selective pulse is minimized to cause selected body regions to be saturated.

21. A method of acquiring signals from blood during magnetic resonance imaging of a subject, said method comprising the steps of:
   placing said subject in a homogeneous, static magnetic field,
   applying a selective presaturation RF pulse to saturate tissue in a first section of the subject wherein it is desired to acquire said signals from inflowing blood, while reducing signals from said tissue in said first section,
   applying a selective RF excitation pulse to another section of the subject wherein it is desired to excite spins in said blood,
   sampling an RF gradient echo signal acquired from the blood entering said first section,
   encoding the first section with encoding pulses applied between said presaturation pulse and said excitation pulse,
   eliminating the encoding from the first section with opposite going encoding pulses applied after said excitation RF pulse and prior to acquiring said sampled signal, which leaves said sampled signal encoded and eliminates encoding from the signals from said saturated first section, said signals that are not encoded generating a line along the read out direction in the image, and removing the line.

22. The method of claim 21 wherein said step of removing the line comprises the steps of:

generating a phase shift of $\pi$ radians on the encoding pulses and on the opposite going encoding pulses which shifts the signals from the first section by $2\pi$ radians and the signals from the other section by $\pi$ radians, and further shifting signals from the first section and the other section after acquisition by $\pi$ radians to shift the line by half the field of view to the edge of the image whereas the signals from the other section are effectively not shifted and provide a normal image.

* * * * *

UNITED STATES PATENT AND TRADEMARK OFFICE
CERTIFICATE OF CORRECTION

PATENT NO. : 5,842,989
DATED : December 1, 1998
INVENTOR(S): Yuval ZUR

It is certified that error appears in the above-identified patent and that said Letters Patent is hereby corrected as shown below:

Col. 2 line 28 delete "suppression pulse such as a"
insert instead (sometimes/referred to herein as "flip angles")--.

Col. 10 line 14 change "encoding" to --encodings--.

Signed and Sealed this

Thirtieth Day of March, 1999

Attest:

Q. TODD DICKINSON

Attesting Officer   Acting Commissioner of Patents and Trademarks